(12) United States Patent
Chopra et al.

(10) Patent No.: US 6,375,937 B1
(45) Date of Patent: Apr. 23, 2002

(54) ANTIPERSPIRANT SALTS FOR ENHANCED COSMETIC PRODUCTS

(75) Inventors: Suman Chopra, Dayton; Xiaozhong Tang, Bridgewater; Peter Hilliard, Jr., Far Hills, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/693,231

(22) Filed: Oct. 20, 2000

(51) Int. Cl.[7] .............................. A61K 7/37; A61K 7/34; A61K 7/38; A61K 7/00
(52) U.S. Cl. ............................. 424/65; 424/66; 424/68; 424/400; 424/401
(58) Field of Search ............................. 424/65, 66, 68, 424/400, 401

(56) References Cited

U.S. PATENT DOCUMENTS

| 4,331,609 A | 5/1982 | Orr |
| 4,871,525 A | 10/1989 | Giovanniello et al. |
| 6,066,314 A | 5/2000 | Tang et al. |
| 6,126,928 A | 10/2000 | Swaile |

FOREIGN PATENT DOCUMENTS

| CA | 1153313 | 9/1983 |
| EP | 0047650 A2 | 3/1982 |
| GB | 2076289 A | 12/1981 |
| WO | WO 99/51192 | 10/1999 |

*Primary Examiner*—Shelley A. Dodson
(74) *Attorney, Agent, or Firm*—Rosemary M. Miano

(57) ABSTRACT

This invention comprises aluminum zirconium salts which have a metal to chloride molar ratio in the range of 0.9–1.2:1 and a glycine:zirconium molar ratio greater than 1.3:1 and antiperspirant compositions made with such salts.

8 Claims, No Drawings

ANTIPERSPIRANT SALTS FOR ENHANCED COSMETIC PRODUCTS

FIELD OF THE INVENTION

This invention relates to a class of antiperspirant salts that may be used to formulate antiperspirants with enhanced efficacy.

BACKGROUND OF THE INVENTION

A variety of art is available that describes various salts and methods of making them. U.S. Pat. No. 4,331,609 to Orr teaches an antiperspirant active comprising aluminum and zirconium made with separate aluminum and zirconium compounds as well as a neutral amino acid wherein the molar ratio of neutral amino acid to total metal is from about 0.90 to about 0.24. The total metal:chlorine ratio in the complex that is formed is less than 1.30.

EP publication number 0 047 650 describes aqueous solution-stable antiperspirant complexes comprising an aluminum compound, a zirconium or hafnium compound, a water soluble neutral amino acid and an inorganic acid. The molar ratio of neutral amino acid to total metal is from about 0.90 to about 0.24 in an aqueous system, and the molar ratio of neutral amino acid to total metal is from about 0.90 to about 0.75 in a non-aqueous system. The total metal:chlorine ratio in the complex that is formed is less than 1.30.

United Kingdom Patent Application GB 2,076,289 describes an antiperspirant compositions comprising a combination of an aluminum chloride and an aluminum zirconium hydroxychloride in a synergistic mixture. The metal:chloride ratio is less than 0.9.

Canadian Patent 1,153,313 describes an antiperspirant composition which contains a buffering agent such as glycine with a synergistic mixture of aluminum chlorohydrate, aluminum chloride or aluminum zirconium polychlorohydrate complex. The molar ratio of aluminum to chloride is in the range of 0.78:1 to abut 1.95:1. Various salts are described which have a metal:halide ratio of 2.1:1–0.9:1. The glycine:zirconium ratio is much less than 1:1.

U.S. Pat. No. 4,871,525 to Giovanniello et al describes a solid powder of aluminum zirconium hydroxyl halide glycinate complex having improved antiperspirant activity wherein the glycine is used to prevent gel formation. The ratio of Zr to glycine is less than 1:1.

U.S. Pat. No. 6,126,928 to Swaile describes antiperspirant compositions wherein the molar ratio of neutral amino acid to total metal (aluminum•zirconium) is from about 0.90 to about 0.24, and the mole ratio of (aluminum•zirconium):chlorine is less than about 1.30:1.

U.S. Pat. No. 6,066,314 to Tang describes the use of post added glycine to aluminum zirconium salts in an amount in the range of 1:1.2–1:5 of zirconium:amino acid on a weight:weight basis.

None of the above cases described the combination of metal to chloride in combination with the glycine to zirconium ratio as found in the instant invention. Thus, it is surprising that the antiperspirant actives described in this invention provide more efficacious cosmetic products.

BRIEF SUMMARY OF THE INVENTION

This invention comprises aluminum zirconium salts which have a metal to chloride molar ratio in the range of 0.9–1.2:1 and a glycine:zirconium molar ratio greater than 1.3:1, particularly greater than 1.4:1.

DETAILED DESCRIPTION OF THE INVENTION

This invention comprises an aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium ratio greater than 1.3:1, particularly greater than 1.4:1.

The salts of this invention may be made in a variety of ways:

Method A:
An aluminum chlorohydrate (ACH) solution of ACH salt in water of suitable concentration is mixed with an aqueous solution of zirconyl chloride ($ZrOCl_2$) of suitable concentration and powdered glycine. The mixture is stirred at room temperature to obtain the salt.

Method B:
A suitable commercially available aluminum zirconium tetrachlorohydrex glycine salt is obtained and mixed with a sufficient amount of an aqueous aluminum chloride ($AlCl_3$) solution and powdered glycine. The mixture is stirred at room temperature to obtain the salt.

When Method B is used, a suitable salt to use as a starting material includes various types of tetra salts such as aluminum zirconium tetrachlorohydrex gly, aluminum zirconium tetrachlorohydrex gly propylene glycol complex aluminum zirconium tetrachlorohydrex gly dipropylene glycol complex, and mixtures of any of the foregoing.

Method C:
An aqueous aluminum chlorohydrate (ACH) solution made from an activated ACH salt of suitable concentration is mixed with an aqueous solution of zirconyl chloride ($ZrOCl_2$) of suitable concentration and powdered glycine. The mixture is stirred at room temperature for a short period of time and then spray dried to obtain the salt in powder form.

If the product is used as a solid powder, the size of the particles of antiperspirant active of the invention currently does not appear to be critical and may include conventional sizes such as greater than 2 to 100 microns, with selected grades having an average particle size of 30–40 microns; finer sized grades having an average particle size distribution from 2–10 microns with average size of about 7 microns as made by a dry-grinding method; and micronized grades of the type described in a co-pending patent application U.S. Ser. No. 9/579,322 having an average particle size of less than or equal to 2 microns, particularly less than or equal to 1.5 microns.

The enhanced salts of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions.

It is preferred that the glycol content of the formulations be kept to a minimum.

Examples of suitable formulations include the following.

Sticks

Stick products may be made with conventional gelling agents such as stearyl alcohol and dibenzylidene sorbitol. A sample formulation is as follows:

40–55% (particularly 45%) cyclomethicone (especially D5 cyclomethicone)
20–30% (particularly 21%) stearyl alcohol
7–15% (particularly 10%) talc 15–22% (particularly 22%) antiperspirant active in powder form 1–3% (particularly 2%) fragrance Roll-Ons 45–65% (particularly 55%) cyclomethicone (especially D5 cyclomethicone)

0.1–10% (particularly 3%) cyclomethicone/dimethicone copolyol (such as Dow Corning 2-5185 C)

10–25% (particularly 20%) antiperspirant active in solution form (25–45% actives on an anhydrous basis in water)

5–30% (particularly 20%) water

1–3% (particularly 2%) fragrance

Soft solids

Soft solids may be made with formulations described in co-pending patent application (U.S. Ser. No. 9/273,152 and PCT Publication number WO 99/51192. A sample formulation is as follows:

40–70% (particularly 50%) elastomer in cyclomethicone (KSG-15 from Shin-Etsu)

5–15% (particularly 6%) polyethylene (for example, beads having a density in the range of 0.91–0.98 g/cm$^3$ and an average particle size in the range of 5–40 microns)

10–20% (particularly 15%) C12-15 alkylbenzoate (Finsolv TN from Finetex)

0.1–25%% (particularly 22%) antiperspirant active in powder form

1–15% (particularly 5%) dimethicone (100 centistokes)

1–3% (particularly 2%) fragrance

Gels

Gels may be made with a variety of formulations such as

5–50% (particularly 29%) cyclomethicone (particularly D5)

0.1–10% (particularly 3%) cyclomethicone/dimethicone copolyol (such as Dow Corning 2-5185 C)

0–10% (particularly 5%) hydrogenated polyisobutene 250

0–10% (particularly 5%) C12-15 alkylbenzoate (Finsolv TN from Finetex)

0–10% (particularly 5%) dimethicone (100 centistokes)

0.1–25% (particularly 20%) antiperspirant active in powder form or 10–25% (particularly 20%) of active in solution (25–45% actives on an anhydrous basis)

5–50% (particularly 30%) water

1–3% (particularly 2%) fragrance

Note that in the explanation of the invention, where water is listed it is intended to count the contribution of the water present in the antiperspirant solution as part of the overall water content. Thus, water is sometimes listed as part of the actives solution or sometimes listed separately.

In a preferred embodiment the refractive indices of the external and internal phases are matched within 0.005 to obtain a clear product.

Particular formulations of interest include:

Formulation A:

0.5–2.5% dimethicone copolyol (for example, Dow Corning 2-5185C (48%))

55–65% elastomer in cyclomethicone (for example, DC-9040 from Dow Corning Corporation (Midland, Mich.) or KSG-15 from Shin-Etsu Silicones of America (Akron, Ohio))

1–10% PPG-3 myristyl ether

10–25% antiperspirant active of the invention

10–25% water 0.5–1.5% fragrance

Formulation B 1.0–3.0% dimethicone copolyol (for example, Dow Corning 2-5185C (48%))

40–60% elastomer in cyclomethicone (for example, DC-9040 from Dow Corning Corporation (Midland, Mich.) or KSG-15 from Shin-Etsu Silicones of America (Akron, Ohio))

1–5% cyclomethicone (in addition to that found in the elastomer)

4–12% PPG-3 myristyl ether

15–30% antiperspirant active of the invention

15–35% water 0.5–1.5% fragrance

Formulation C 1.0–3.0% dimethicone copolyol (for example, Dow Corning 2-5185C (48%))

1–10% hydrogenated polyisobutene (for example, Fancol™ Polyiso 250)

40–55% elastomer in cyclomethicone (for example, DC-9040 from Dow Corning Corporation (Midland, Mich.) or KSG-15 from Shin-Etsu Silicones of America (Akron, Ohio))

3–8% PPG-3 myristyl ether

15–20% antiperspirant active of the invention 20–30% water 1.0–3.0% fragrance

Formulation D 1.0–3.0% dimethicone copolyol (for example, Dow Corning 2-5185C (48%))

40–60% elastomer in cyclomethicone (for example, DC-9040 from Dow Corning Corporation (Midland, Mich.) or KSG-15 from Shin-Etsu Silicones of America (Akron, Ohio))

3–8% PPG-3 myristyl ether

15–30% antiperspirant active of the invention

15–30% water 0.5–1.5% fragrance

1–10% diethylhexyl naphthalate

Formulation E 0.5–2.5% dimethicone copolyol (for example, Dow Corning 2-5185C (48%))

60–70% elastomer in cyclomethicone (for example, DC-9040 from Dow Corning Corporation (Midland, Mich.) or KSG-15 from Shin-Etsu Silicones of America (Akron, Ohio))

7–10% antiperspirant active of the invention

25–35% water

1–10% methylpropylene diol (MPDiol)

0.5–1.5% fragrance

Formulation F 1.0–3.0% dimethicone copolyol (for example, Dow Corning 2-5185C (48%))

6–10% hydrogenated polyisobutene (for example, Fancol™ Polyiso 250)

35–45% elastomer in cyclomethicone (for example, DC-9040 from Dow Corning Corporation (Midland, Mich.) or KSG-15 from Shin-Etsu Silicones of America (Akron, Ohio))

6–10% PPG-3 myristyl ether
40–50% antiperspirant active of the invention as 43% active in water
no additional water
0.5–1.0% fragrance Formulation G
  0.1–0.6% dimethicone copolyol (for example, Dow Corning 2-5185C (48%))
  4–7% hydrogenated polyisobutene (for example, Fancol™ Polyiso 250)
  40–50% elastomer in cyclomethicone (for example, DC-9040 from Dow Corning Corporation (Midland, Mich.) or KSG-15 from Shin-Etsu Silicones of America (Akron, Ohio))
  4–7% PPG-3 myristyl ether
  40–50% antiperspirant active of the invention as 43% active in water
  no additional water
  0.5–1.0% fragrance Formulation H
  0.5–2.0% dimethicone copolyol (for example, Dow Corning 2-5185C (48%))
  1–7% hydrogenated polyisobutene (for example, Fancol™ Polyiso 250)
  40–50% elastomer in cyclomethicone (for example, DC-9040 from Dow Corning Corporation (Midland, Mich.) or KSG-15 from Shin-Etsu Silicones of America (Akron, Ohio))
  45–55% antiperspirant active as 43% active of the invention in water
  no additional water
  0.5–1.5% fragrance Formulation I
  2–7% dimethicone copolyol (for example, Dow Corning 2-5185C (48%))
  0.1–1% Oleath-20
  1–5% C12-15 alkyl benzoate (Finsolv TN)
  15–25% elastomer in cyclomethicone (for example, DC-9040 from Dow Corning Corporation (Midland, Mich.) or KSG-15 from Shin-Etsu Silicones of America (Akron, Ohio))
  15–25% antiperspirant active
  15–30% water
  0.5–1.5% fragrance The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For sticks, sprays, aerosols and roll-ons the compositions can be placed in a conventional types of container (with the inclusion of propellants in aerosols). This provides good deposition of the active material on the skin.

Compositions of the present invention can be formulated as clear, translucent or opaque products, although clear products are preferred. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present invention, there are differences between transparent (clear), translucent and opaque compositions.

The improved efficacy can be evaluated by reference to conductivity tests.

The release of antiperspirant actives into the sweat is a significant event in the development of an antiperspirant effect. The magnitude of the antiperspirant effect is related to the concentration of the antiperspirant salt in the sweat, and therefore measuring the concentration of antiperspirant salt can provide an estimate of antiperspirant efficacy. A variety of methods can be used to evaluate antiperspirant salt concentration, ranging from atomic absorption, ICP, and HPLC to solution conductance of aqueous films. The later method is especially well suited for measuring the release of small amounts of antiperspirant salts. The methods outlined below use solution conductance to estimate antiperspirant salt release upon short exposures to deionized water.

As noted above, the conductance of the compositions of the invention is defined with reference to a value of at least 250 micro Siemens/cm/ml when the composition is loaded with at least 7% of an antiperspirant active (such as the antiperspirant actives listed above) and when the conductance is measured by a fixed geometry test. For purposes of clarification it should be explained that there are a variety of tests and test conditions that can be used to evaluate:

(1) "Conductance" is defined as an absolute measure of current flow through a solution with the dimensions of micro Siemens/cm, which value is independent of probe geometry. This value is divided by the volume (in ml) of applied water to give the conductance number with the units of micro Siemens/cm/ml. This test is deemed a more reproducible measurement since it references a set of fixed dimensions and units.

(2) Alternatively, "conductivity" as a measure of current flow through a solution without reference to probe geometry, and which is measured in micro Siemens. This test is convenient for quick screening of solutions.

Standard Test for Thin Film Conductivity

One test for conductivity is called herein the "standard" test. A non-conducting plastic block (for example, made from PLEXIGLAS® material) to form an oval shaped well 12.2 cm×2.5 cm with a depth of 100 microns. This depth corresponds to the mean thickness of an antiperspirant product applied to the underarm of a human person during real use conditions (approximately 50 to 100 microns). An aliquot of test sample is placed in the well of the block sufficient to fill the well to the brim. Excess sample is scraped off by running a flat edged instrument over the surface of the block. The sample block, with the product film, is then either (a) equilibrated at room temperature for two hours or (b) placed in a synthetic underarm to simulate in vivo conditions. If method (b) is used, the air temperature inside the synthetic underarm is maintained at 33 to 35° C. and a relative humidity of 85 to 95%, and the sample blocks are placed on a temperature controlled surface maintained at body temperature (37° C.). These conditions closely approximate the temperature gradients normally found in the underarm. Samples are equilibrated in either the (a) or (b) environments for two hours prior to measurement of antiperspirant salt release by solution conductivity. After two hours the sample blocks are removed from the controlled environment and placed on a stage for conductivity measurement. An aliquot of 250 microliters of water with a resistance of at least 17 mega ohms is placed on the surface of the sample film, and the conductance of the water is measured as a function of time with a Skicon 200 Skin surface Hygrometer (I.B.S. Co., Ltd., Shizuoka-ken, 430, Japan) using an Elsnau (MT-8C Probe) electrode (Todd Maibach & Associates, San Francisco, Calif.). The electrode is positioned so that it touches the bottom of the test sample in the well. Conductivity is measured in micro Siemens at 3.5 MHz. Data is collected at 0.1 sec intervals for approximately 100 sec. Solution conductivity after 10 seconds of exposure to the water is used to compare the release of active salt for different formulations. This method is believed to be particularly useful for evaluating the release of antiperspirant salts in the absence of other salts. The standard method is useful as a quick screening tool for active salt release studies. A solution conductivity of approximately 400 or greater micro Siemens at 10 sec after application of the water droplet to the surface of the test sample, can be considered evidence of significant release of the antiperspirant active salt from the film surface and correlates with improved antiperspirant efficacy.

Fixed Geometry Test for Thin Film Conductance

One of the limitations of the Standard Test is that the area of the water droplet is not controlled and, therefore, the apparent conductance (which is measured as conductivity because the water volume is not controlled) is dependent on droplet spreading. This will lead to an underestimate of the actual solution conductance (and therefore antiperspirant salt release), of water drops which spread significantly. In order to measure the absolute concentration of the antiperspirant salts the spreading of the water drop must be stopped. This can be accomplished by placing a well of know dimensions on the surface of the product film to establish an area of constant size that is exposed to the water droplet. A more predictable test is needed, such as the Fixed Geometry Test.

The Fixed Geometry Test uses the same basic technique as the Standard Test in terms of preparation of the test well, addition of the test sample and equilibration of the sample to a selected temperature. Instead of allowing the water to flow freely on the surface of the test film, however, a second structure of non-conducing plastic predrilled with holes of a fixed diameter is clamped over the well block. The second structure with holes is also made of a non-conducting material (such as PLEXIGLAS material), is open on both ends and has an internal diameter of 1.905 cm. The bottom of each predrilled hole is fitted with a small O-ring to prevent leakage of the water. A 400 microliter aliquot of water (rather than the 250 microliter aliquot used in the Standard Test) with a resistance of 17 mega Ohms is then placed in the hole to cover the test sample. This will normally result in a liquid height for water of about 1.4 mm. The Elsnau probe is positioned through the drilled hole so that the bottom of the probe rests on the bottom of the well at a right angle. Because of the fixed shape, data can be obtained as conductance in micro Siemens/cm/ml using the method described for calculation.

As will be appreciated by those skilled in the art, a variety of other shapes, sizes and orientations of electrodes can be used. In another variation on the Fixed Geometry Test, thin gold wires (99% purity, set of 2, each about 1 mm in diameter) can be constructed to be in parallel with the surface of the water (and covered by the water) and conductance can be measured.

The electrode used in both types of tests must be calibrated so that a conductivity in micro Siemens can be obtained. Such calibration with a salt solutions in water of known conductance is known to those skilled in the art.

While different readings can be obtained depending on the thickness of the films, the test used, etc. it is important to establish a standard test for purposes of defining conductivity according to this invention. The Fixed Geometry Test is set as the defining test because it is believed to be more reproducible. Thus a minimum conductance value of 250 micro Siemens/cm/ml is the lower limit. Interestingly, minimum values for the Standard Test seemed to run about 400 micro Siemens due to the way the test was conducted. For the data described here, samples should be placed in a chamber at the humidity and elevated temperature conditions described above for about 2 hours. Samples not subjected to elevated temperatures should give higher values.

An average efficacy gel having a water content of greater than 35% (such as Gillette's Right Guard Antiperspirant Gel) was compared with an improved gel made according to Example 12 below. The average efficacy gel has a standard conductivity of 295±35 micro Siemens at 10 seconds and a fixed geometry conductivity of 121±47 micro Siemens/cm/ml at 10 seconds. The improved formulation made according to this invention (Example 21) had a standard conductivity of 4526 micro Siemens at 10 seconds. The improved formulation was ranked as above average in efficacy in a forearm test whereas the average gel was ranked as average in efficacy in a clinical test.

It is believed that the more homogeneous the composition is and the more uniform the particle size, the better properties of the composition.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

EXAMPLES

The following Examples are offered as illustrative of the invention and are not to be construed as limitations thereon.

In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. If alcohol is used, it is 95% unless otherwise indicated. Unless otherwise indicated, "water" or "D.I. water" mean deionized water. As is true throughout the application, the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., $7^{th}$ ed. 1997). While specific amounts of particular elastomers have been described, there are chemical differences in the variety of elastomers that are available. The use of different elastomers may result in the need to increase or decrease the amount of elastomer used in a particular formulation, especially if a clear product is desired.

In the Examples, as elsewhere in the description of the invention, reference is made to using the antiperspirant active either as a powder or in some type of solution such as dissolved in water at a concentration or 25–45% actives on an anhydrous basis.

Examples 1–4

Antiperspirant Salts

Improved aluminum zirconium tetrachlor hydrex gly salt can be made using the following Examples 1–3. The goal is to enhance the smallest Al species (Peak-5) by lowering the metal:chloride molar ratio of the tetra-salt to be in the range of 1.2–0.9:1 and to raise the glycine/Zr molar ratio to be greater than 1.3.

Example 1

Glycine powder (159 g) is added to a zirconium compound (1000 g of a 31% solution of zirconium oxychloride ($ZrOCl_2$)) with stirring. Aluminum chlorohydrate ("ACH") (1120 g of a 50% aqueous ACH solution) is then added with additional stirring. The final solution is then diluted with distilled water into an anhydrous concentration of 33.0%, with a glycine/zirconium molar ratio of 1.45:1; aluminum/zirconium molar ratio of 3.56:1, and metal/chloride ratio of 1.01:1.

Example 2

Glycine powder (159 g) is added to a zirconium compound (1000 g of a 31% solution of zirconium oxychloride ($ZrOCl_2$) with stirring. ACH (1204 g of a 50% aqueous ACH solution) is then added with additional stirring. The final solution is then diluted with distilled water into an anhydrous concentration of 30.0% with a glycine/zirconium molar ratio as 1.45:1; an aluminum/zirconium molar ratio of 3.82:1, and a metal/chloride ratio of 0.98.

Example 3

A solution of $AlCl_3$ (200 g of 28% aqueous solution) is added to a ZAG solution (800 g of a 43% solution of Westchlor Zr 35BX3) with stirring. The mixture is then diluted into an anhydrous concentration of 30%. The final solution has an aluminum/zirconium molar ratio of 4.36:1; a metal/chloride ratio of 0.94:1; and a glycine/zirconium ratio of 0.97:1.

Example 4

Glycine powder (159 g) is added to a zirconium compound (1000 g of a 31% solution of zirconium oxychloride ($ZrOCl_2$)) with stirring. Aluminum chlorohydrate ("ACH") (2800 g of a 20% ACH solution made from a powder (REACH 101, from Reheis, Berkeley Height, N.J.) is then added with additional stirring. The final solution is then quickly spray dried to remove water. The ZAG powder obtained has a glycine/zirconium molar ratio of 1.42:1; an aluminum:zirconium molar ratio of 3.56:1; and a metal:chloride ratio of 1.05:1.

Analytical Data for Examples 1–3

Size exclusion chromatography ("SEC") or gel permeation chromatography ("GPC") are methods frequently used for obtaining information on polymer distribution in antiperspirant salt solutions. With appropriate chromatographic columns, at least five distinctive groups of polymer species can be detected in a ZAG, appearing in a chromatogram as peaks 1, 2, 3, 4 and a peak known as "5,6". Peak 1 is the larger Zr species (greater than 120–125 A). Peaks 2 and 3 are larger aluminum species. Peak 4 is smaller aluminum species (aluminum oligomers) and has been correlated with enhanced efficacy for both ACH and ZAG salts. Peak 5,6 is the smallest aluminum species. The relative retention time ("Kd") for each of these peaks varies depending on the experimental conditions. Data for Table A was obtained using the SEC method described in an issued patent owned by the same company as a this case, U.S. Pat. No. 6,066,314, incorporate by reference as to the test method described therein.

TABLE A

Polymer distribution of the improved ZAG samples: (SEC analysis)

| | Peak-1/Peak-3 | Peak-2/Peak-3 | Peak-4/Peak-3 | Peak-5/Peak-3 |
|---|---|---|---|---|
| Example 1 | 0 | 0.2 | 0.24 | 3.11 |
| Example 2 | 0 | 0.03 | 0.17 | 1.71 |
| Example 3 | 0.95 | 0.34 | 0.27 | 2.60 |

Example 10

General Method for Making Antiperspirant Products

In general, the external and internal phases are formed separately either at room temperature or with heating as described below. The internal phase is added to the external phase very slowly while stirring at to form an emulsion. After the addition has been completed, the mixture is stirred at higher speed to achieve a homogeneous mixture. The final formula viscosity is then achieved by homogenizing the emulsion under either batch or continuous process conditions as described below. The fragrance may be added at any time during the process prior to final homogenization.

Preparation of the external phase:

The ingredients to be used in the external phase (including the elastomer) are weighed out at room temperature and combined in a suitable vessel such as a 2 liter glass beaker. The mixture is stirred at about 500 rpm for 15–20 minutes using an overhead mixer such as a Lightnin Mixer Model 1.1003. If a waxy or solid emollient is to be added to the external (also called "continuous") phase, the mixture may be heated to facilitate dissolution while stirring then cooled to room temperature prior to combination with the internal phase as described below. The elastomer component is obtained as a suspension of elastomer in cyclomethicone (for example at a concentration of 6% active in D5 cyclomethicone). The elastomer component is added to the external phase with stirring at high speed (500–700 rpm for a 0.5 kilogram batch) until no particles of elastomer are visible to the eye.

Preparation of the internal phase:

The internal dispersed phase is prepared as described below. Ingredients are mixed for a time sufficient to achieve homogeneity. The antiperspirant active used is weighed into a large beaker equipped with an overhead stirrer. Other internal phase ingredients are then added while stirring.

The fragrance (if any is used) is added last and may be added either to the internal phase or the external phase or the final formula prior to homogenization. For many of the examples described here, one could add the fragrance to the internal phase.

If an optional non-ionic emulsifier such as Oleath-20 is used, the emulsifier and propylene glycol are combined in a separate beaker and heated to 40 degrees C. with stirring until the non-ionic emulsifier completely dissolved. The heat is turned off and the remaining ingredients to be used in the internal phase, including the antiperspirant active are weighed out and added to the mixture of propylene glycol and non-ionic emulsifier.

If water or a salt solution are used, the internal phase is prepared as follows. The solution containing antiperspirant active salt as received from supplier is weighed into a large beaker equipped with a magnetic stirrer. Additional ingredients such as propylene glycol, ethanol and water are added while stirring. If a salt water solution is used (such as for NaCl, etc.), the salt water solution is prepared by dissolving the crystalline salt in water in a separate beaker and stirring until dissolved. The salt water solution is then added to the rest of the internal phase and the mixture is stirred until homogeneous.

Preparation of the Emulsion:

The internal phase made as described above is then added to the external phase over the course of 15–30 minutes while stirring at a speed of 500–700 rpm. After the addition is complete, the mixture is stirred at 500–700 rpm for 20 minutes using a Lightnin Mixer Model 1.1003. The mixture is then homogenized for 2–4 minutes (especially 3 minutes) using a homogenizer from Greerco Corp., Hudson, N.H. at a reading of about 60 on a Powerstat Variable Autotransformer from Superior Electric Co., Bristol, Ct.

Further Processing:

The product is then further processed by homogenization to achieve the desired final viscosity. This can be done by using a Gilford-Wood Model 1-L (Greerco Corp., Hudson, N.H.) homogenizer. The homogenizer speed is controlled by a Powerstat Variable Autotransformer Type 3PN116B (Superior Electronic. Co., Bristol, Ct.). Typical voltage setting and processing time are chosen to give a desired final formula viscosity.

An other method of homogenization of the final product is to pass the emulsion through a colloid mill such as a Sonic Tri-Homo Colloid Mill or a process sonolator such Sonic Production Sonolator 200-30 both available from Sonic Corporation of Stratford, Ct. Process conditions are chosen to give the desired final product viscosity.

Examples 13–22 and 24–34

Compositions

The method described in Example 1 may be used to make the compositions listed in Tables B and C with the types and amounts of ingredients listed in the Tables. Amounts are in percent by weight based on the total weight of the composition. For Examples 13–16, 24, 25, 27 and 34, a powder form of the active may be used. For Examples 17–21, 28 and 30 a solution of 25–45% actives on an anhydrous basis may be used. For Example 22, 26 and 29, an active material prepared according to Example 1 is used as a 41.28% actives (on an anhydrous basis) solution in water. For Examples 31 and 33 an active material prepared according to Example 1 is used as a 33% actives (on an anhydrous basis) solution in water. For Example 32 an active material prepared according to Example 1 is used as a 31.16% actives (on an anhydrous basis) solution in water.

TABLE B

| Ingredient | Ex. 13 | Ex. 14 | Ex. 15 | Ex. 16 | Ex. 17 | Ex. 18 | Ex. 19 | Ex. 20 | Ex. 21 | Ex. 22 |
| --- | --- | --- | --- | --- | --- | --- | --- | --- | --- | --- |
| External Phase | | | | | | | | | | |
| Elastomer (KSG-15, 6% active) | 62 | 50 | 48 | 40 | 41.5 | 42.0 | 46.5 | 35 | 32.17 | 25 |
| Dimethicone copolyol (Dow Corning 2-5185, 48% active in cyclomethicone) | 2 | 2 | 1.5 | 4 | 1.5 | 0.5 | 1.0 | 1.0 | 2.48 | 1.0 |
| Hydrogenated polyisobutene (Polyiso 250) | 0 | 0 | 5 | 8 | 5 | 5 | 5 | 5 | 4.95 | 0 |
| PPG-3 Myristyl Ether | 5 | 5 | 4.5 | 0 | 4.5 | 5.0 | 0 | 0 | 0 | 5 |
| C12–15 alkyl benzoate (FINSOLV IN) | | | | 2.0 | | | | | | |
| Cyclomethicone (Dow Corning 245) | 0 | 2 | 0 | 0 | 0 | 0 | 0 | 0 | 0 | 0 |
| Fragrance | 1 | 1 | 1 | 1 | 1 | 1 | 1 | 1 | 1 | 0 |
| Interal Phase | | | | | | | | | | 0 |
| Antiperspirant Active[a] | 15 | 20 | 17.5 | 19.5 | 46.5 | 46.5 | 46.5 | 58 | 59.40 | 48.45 |
| Water (deionized)[b] | 15 | 20 | 22.5 | 25 | 0 | 0 | 0 | 0 | 0 | 0 |
| Oleath-20 (HLB-8) | 0 | 0 | 0 | 0.5 | 0 | 0 | 0 | 0 | 0 | 19.55 |
| Total | 100 | 100 | 100 | 100 | 100 | 100 | 100 | 100 | 100 | 100 |

[a]Any of the actives described in Examples 1–4 may be used.
[b]Note that in the examples, sometimes the antiperspirant active is listed as a solution (which will include a water component) under the "active" designation with little or no water and sometimes the active and water are listed separately.

TABLE C

| Ingredient | Ex. 24 | Ex. 25 | Ex. 26 | Ex. 27 | Ex. 28 | Ex. 29 | Ex. 30 | Ex. 31 | Ex. 32 | Ex. 33 | Ex. 34 |
|---|---|---|---|---|---|---|---|---|---|---|---|
| External Phase | | | | | | | | | | | |
| Elastomer (DC 9040) 12% active) | 55 | 62 | 62 | 40 | 41.5 | 25 | 31.5 | 21 | 17 | 17 | 50 |
| Dimethicone copolyol (Dow Corning 2-5185, 48% active in cyclomethicone) | 1 | 2 | 2 | 4 | 1 | 1 | 2.5 | 1 | 1 | 1 | 2 |
| Hydrogenated polyisobutene (Polyiso 250) | 5 | — | — | 8 | 5 | — | 5 | 1.5 | 1.5 | 1.5 | — |
| PPG-3 Myristyl Ether | 3 | 4.5 | 5 | — | 5 | 5 | — | 0.5 | 0.5 | 0.5 | 5.0 |
| C12–15 alkyl benzoate (FINSOLV TN) | — | — | — | 2 | — | — | — | — | — | — | — |
| Cyclomethicone (Dow Corning 245) | — | — | — | — | — | — | — | 5 | 9.0 | 9.0 | 2.0 |
| Fragrance | 1 | 1 | 1 | 1 | 1 | 1 | 1 | 1 | 1 | 1 | 1 |
| Internal Phase | | | | | | | | | | | |
| Antiperspirant Active[a] | 15 | 15.5 | 30 | 19.5 | 46.5 | 48.45 | 60.0 | 60.5 | 63.68 | 60.13 | 20 |
| Water (deionized)[b] | 20 | 15 | | 25 | | 19.55 | | 9.5 | 6.32 | 9.87 | 20 |
| Oleath-20 (HLB-8) | — | — | — | 0.5 | — | — | — | — | — | — | — |
| Total | 100 | 100 | 100 | 100 | 100 | 100 | 100 | 100 | 100 | 100 | 100 |

[a]See explanation of actives used. Actives according to Examples 1–4 may be used.
[b]Note that in the examples, sometimes the antiperspirant active is listed as a solution (which will include a water component) under the "active" designation with little or no water and sometimes the active and water are listed separately.

Examples 13–22 and 24–34

Conductivity

The Standard Method described above may be used with a 250 microliter drop of water placed on a 100 micron thick film of the test formula. Before the test each sample was equilibrated for 2 hours at 35 degrees C. and 85% relative humidity (simulation of underarm conditions). If the Fixed Geometry Method is not used to obtain conductance data, for the listed Examples, the diameter of the spreading of the water drop is given. As noted above a minimum of 250 micro Siemens for the Fixed Geometry Method is the defined lower limit. Readings for conductivity using the Standard Method will be somewhat higher. The Control Gel Example was prepared using the same procedure as described for Examples 13–33 with 5% dimethicone copolyol (Dow Corning 2-5185 diluted to 40%); 1% Cyclomethicone (DC 245 (D5)); 53.37% antiperspirant active (28% in propylene glycol) (Westchlor 4105); 6.08% propylene glycol; 9.12% alcohol (SDA 40 200); 1.0% fragrance; 0.23% Tween 80; and 8.5% elastomer (5.8% actives in D5 cyclomethicone—elastomer described in U.S. Pat. No. 6,060,546). The Control Stick Example was Lady Speed Stick. The data shows that emulsion of the invention has conductivity as good as or better than the stick.

The samples may be prepared by matching the RI's of the two phases (within 0.005) and samples were visually observed to be clear.

Conductivity for the Examples in TABLES B and C was evaluated using the Standard Method. The results are listed in TABLE D.

TABLE D

| Property | Ex. 22 | Ex. 26 | Ex. 29 | Ex. 32 | Ex. 33 |
|---|---|---|---|---|---|
| Diameter of water droplet after spreading (cm) | 5.03 | 1.3 | 5.4 | 4.8 | 3.1 |
| Conductivity at 10 seconds (micro Siemens) | 4526 | 547 | 4511 | 4842 | 3554 |
| % oil phase | 30 | 70 | 32 | 30 | 30 |

The data in Table D may be compared with the data in Table E which is data for controls. Control stick #1 is Lady Speed Stick® antiperspirant (Mennen), and Control stick #2 is Right Guard® antiperspirant (Gillette). Normally a gel product does not have very good conductivity while stick products have much better conductivity. The data in Table F shows that compositions of the present invention have conductivity values comparable to stick products.

TABLE E

| Property | Control Gel #1 | Control Stick #1 | Control Gel #2 |
|---|---|---|---|
| Diameter of water droplet after spreading (cm) | 0.87 | 1.7 | 1.2 |
| Conductivity at 10 seconds (micro Siemens) | 154 | 1627 | 295 |
| % oil phase | 30 | (suspension) | 20 |

We claim:

1. An aluminum zirconium tetrachlorohydrex glycine salt having a metal to chloride molar ratio in the range of 0.9–1.2:1; and a glycine:zirconium molar ratio greater than 1.3:1.

2. An aluminum zirconium tetrachlorohydrex glycine salt according to claim 1 wherein the glycine:zirconium molar ratio is greater than 1.4:1.

3. An aluminum zirconium tetrachlorohydrex glycine salt according to claim 1 wherein the metal to chloride molar ratio is in the range of 0.9–1.1:1.

4. An aluminum zirconium tetrachlorohydrex glycine salt according to claim 2 wherein the metal to chloride molar ratio is in the range of 0.9–1.1:1.

5. An antiperspirant composition made with an aluminum zirconium tetrachlorohydrex glycine salt having a metal to chloride molar ratio in the range of 0.9–1.2:1; and a glycine:zirconium molar ratio greater than 1.3:1.

6. An antiperspirant composition according to claim 5 wherein the aluminum zirconium tetrachlorohydrex glycine salt has a glycine:zirconium molar ratio greater than 1.4:1.

7. An antiperspirant composition according to claim 5 wherein the metal to chloride molar ratio of the aluminum zirconium tetrachlorohydrex glycine salt is in the range of 0.9–1.1:1.

8. An antiperspirant composition according to claim 7 wherein the metal to chloride molar ratio of the aluminum zirconium tetrachlorohydrex glycine salt is in the range of 0.9–1.1:1.

* * * * *

UNITED STATES PATENT AND TRADEMARK OFFICE
CERTIFICATE OF CORRECTION

PATENT NO. : 6,375,937 B1
DATED : April 23, 2002
INVENTOR(S) : Suman Chopra, Sheridan Tang and Peter Hilliard, Jr.

It is certified that error appears in the above-identified patent and that said Letters Patent is hereby corrected as shown below:

<u>Column 13,</u>
Table D, please change the word "Diameter" to -- Area --.
Table D, please change "(cm)" to -- (cm$^2$) --.

<u>Column 14,</u>
Table E, please change the word "Diameter" to -- Area --.
Table E, please change "(cm)" to -- (cm$^2$) --.

Signed and Sealed this

Twenty-sixth Day of November, 2002

*Attest:*

*Attesting Officer*

JAMES E. ROGAN
*Director of the United States Patent and Trademark Office*

(12) EX PARTE REEXAMINATION CERTIFICATE (4990th)
United States Patent
Chopra et al.

(10) Number: US 6,375,937 C1
(45) Certificate Issued: Sep. 14, 2004

(54) ANTIPERSPIRANT SALTS FOR ENHANCED COSMETIC PRODUCTS

(75) Inventors: Suman Chopra, Dayton, NJ (US); Xiaozhong Tang, Bridgewater, NJ (US); Peter Hilliard, Jr., Far Hills, NJ (US)

(73) Assignee: Colgate-Palmolive Company, New York, NY (US)

Reexamination Request:
No. 90/006,415, Oct. 15, 2002

Reexamination Certificate for:
Patent No.: 6,375,937
Issued: Apr. 23, 2002
Appl. No.: 09/693,231
Filed: Oct. 20, 2000

Certificate of Correction issued Nov. 26, 2002.

(51) Int. Cl.[7] ............. A61K 7/37; A61K 7/34; A61K 7/38; A61K 7/00

(52) U.S. Cl. ............. 424/65; 424/66; 424/68; 424/400; 424/401

(58) Field of Search ................. 424/65, 66, 68, 424/400, 401

(56) References Cited

U.S. PATENT DOCUMENTS 2,814,585 A * 11/1957 Daley .................. 424/66
3,981,986 A * 9/1976 Rubino ................. 424/47
5,997,850 A * 12/1999 Tang et al. ............ 424/65

OTHER PUBLICATIONS

Reheis data sheet for Reach AZP–902 and 855, 1997.*

* cited by examiner

*Primary Examiner*—Thurman K. Page

(57) ABSTRACT

This invention comprises aluminum ziconium salts which have a metal to chloride molar ratio in the range of 0.9–1.2:1 and a glycine:zirconium molar ratio greater than 1.3:1 and antiperspirant compositions made with such salts.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–8 are cancelled.

* * * * *